United States Patent
Ye et al.

(10) Patent No.: US 12,159,410 B2
(45) Date of Patent: Dec. 3, 2024

(54) IMAGE SEGMENTATION METHOD USING NEURAL NETWORK BASED ON MUMFORD-SHAH FUNCTION AND APPARATUS THEREFOR

(71) Applicant: Korea Advanced Institute of Science and Technology, Daejeon (KR)

(72) Inventors: JongChul Ye, Daejeon (KR); Boah Kim, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 518 days.

(21) Appl. No.: 17/376,588

(22) Filed: Jul. 15, 2021

(65) Prior Publication Data
US 2022/0020155 A1    Jan. 20, 2022

(30) Foreign Application Priority Data

Jul. 16, 2020   (KR) .......................... 10-2020-0087870
Nov. 19, 2020  (KR) .......................... 10-2020-0155965

(51) Int. Cl.
G06K 9/00   (2022.01)
G06N 3/08   (2023.01)
G06T 7/10   (2017.01)

(52) U.S. Cl.
CPC ................. *G06T 7/10* (2017.01); *G06N 3/08* (2013.01); *G06T 2207/20081* (2013.01); *G06T 2207/20084* (2013.01)

(58) Field of Classification Search
CPC ............. G06T 7/10; G06T 2207/20081; G06T 2207/20084; G06T 7/11; G06N 3/08; G06N 3/045; G06N 3/048; G06N 3/084; G06N 3/088; G16H 30/40; G16H 50/20
See application file for complete search history.

(56) References Cited

U.S. PATENT DOCUMENTS

2020/0272888 A1*   8/2020   Wang ................... G06V 40/103
2021/0150329 A1*   5/2021   Rhodes .................... G09G 3/00

FOREIGN PATENT DOCUMENTS

KR           20190024636 A   *   3/2019

OTHER PUBLICATIONS

Yanchao Yang, Unsupervised Moving Object Detection viaContextual Information Separation, 2019, CVPR.*
Xu Ji, Invariant Information Clustering for Unsupervised Image Classification and Segmentation, IEEE Xplore, 2019.*
Boah Kim, Jong Chul Ye, "Mumford-Shah Loss Functional for Image Segmentation with Deep Learning", Sep. 9, 2019, IEEE Transactions on Image Processing (vol. 29).
Boah Kim, Jong Chul Ye, "Mumford-Shah Loss Functional for Image Segmentation with Deep Learning", Sep. 27, 2019, IEEE Transactions on Image Processing (vol. 29).

(Continued)

*Primary Examiner* — Xin Jia
(74) *Attorney, Agent, or Firm* — ArentFox Schiff LLP; Joseph M. Maraia; Marlo S. Grolnic

(57) ABSTRACT

Disclosed is an image segmentation method including receiving an image to be segmented and segmenting the received image by using a neural network learned through a Mumford-Shah function-based loss function.

13 Claims, 7 Drawing Sheets

FIG. 3B

(56) References Cited

OTHER PUBLICATIONS

S. Afshari et al, "Weakly Supervised Fully Convolutional Network for PET Lesion Segmentation", Medical Image Analysis Lab, School of Computing Science, Simon Fraser University, Canada, Mar. 2019, DOI:10.1117/12.2512274, (8 pages).
Ye, Jong Chul et al, "Deep Convolutional Framelets: a General Deep Learning Framework for Inverse Problems", Society for Industrial and Applied Mathematics, vol. 11, No. 2, pp. 991-1048, Apr. 24, 2018, http://www.siam.org/journals/siims/11-2/M114177. html, (58 Pages).
Korean Office Action issued Sep. 6, 2022, for related Application No. 10-2020-0155965 (Korean language version).

\* cited by examiner

IMAGE SEGMENTATION METHOD USING NEURAL NETWORK BASED ON MUMFORD-SHAH FUNCTION AND APPARATUS THEREFOR

CROSS-REFERENCE TO RELATED APPLICATIONS

This application claims priority under 35 U.S.C. § 119 to Korean Patent Application No. 10-2020-0087870 filed on Jul. 16, 2020 and Korean Patent Application No. 10-2020-0155965 filed on Nov. 19, 2020 in the Korean Intellectual Property Office, the disclosures of which are incorporated by reference herein in their entireties.

BACKGROUND

Embodiments of the present disclosure described herein relate to an image segmentation technology using a Mumford-Shah function-based neural network, and more particularly, relate to an image segmentation method capable of segmenting an image by using a neural network learned through a Mumford-Shah function-based loss function, and an apparatus therefor.

Image segmentation refers to assigning labels to all pixels within a specific region in an image. As an image segmentation technology is used indispensably in various application fields such as object detection and medical image analysis, the image segmentation technology is being studied centrally in a field of computer vision. Nowadays, the performance of the deep learning-based image segmentation method is very good, and related research is continuously being developed. Most image segmentation methods refer to supervised learning-based methods using convolutional neural networks (CNNs). However, the supervised learning method requires a large amount of data with high-quality pixel-level labels for each image, and thus it takes a lot of time to obtain data. In particular, it may be difficult to obtain a label for a specific image such as a medical image. To solve the issues, a semi-supervised learning-based image segmentation method has been recently developed. The semi-supervised learning-based image segmentation method refers to a method using an image-unit label, a region box label, or a small amount of pixel-unit label.

In the meantime, a conventional image segmentation method minimizes a specific energy function for a given image. Accordingly, objects constituting an image based on unsupervision may be clustered into several categories. This method enables pixel-unit estimation without labels for image segmentation regions. However, there is a limit in segmenting an image such as a tree and a car, which needs a lot of computation and has the meaning for semantics (i.e., a segmentation region).

SUMMARY

Embodiments of the present disclosure provide an image segmentation method capable of segmenting an image by using a neural network learned through a Mumford-Shah function-based loss function, and an apparatus therefor.

According to an embodiment, an image segmentation method includes receiving an image to be segmented and segmenting the received image by using a neural network learned through a Mumford-Shah function-based loss function.

The neural network may be learned based on one of supervised learning, semi-supervised learning, and unsupervised learning.

When the neural network is learned based on supervised learning, the neural network may use the Mumford-Shah function-based loss function as a regularization function.

The neural network may be learned based on the Mumford-Shah function-based loss function and a loss function using pixel-unit labels.

The segmenting may include outputting a segmentation map for the received image by using the neural network and segmenting the received image by using the output segmentation map.

The segmenting may include outputting a segmentation map, to which a bias value of the received image is reflected, by using the neural network and segmenting the received image by using the output segmentation map.

The Mumford-Shah function-based loss function may be a loss function that performs computation using only an input image without a label.

The neural network may include a convolution framelet-based neural network and a neural network including a pooling layer and an unpooling layer.

According to an embodiment, an image segmentation method includes defining a Mumford-Shah function-based loss function, learning a neural network by using the defined Mumford-Shah function-based loss function, receiving an image to be segmented, and segmenting the received image by using the neural network learned through the Mumford-Shah function-based loss function.

According to an embodiment, an image segmentation apparatus includes a receiving unit that receives an image to be segmented and a segmenting unit that segments the received image by using a neural network learned through a Mumford-Shah function-based loss function.

The neural network may be learned based on one of supervised learning, semi-supervised learning, and unsupervised learning.

When the neural network is learned based on supervised learning, the neural network may use the Mumford-Shah function-based loss function as a regularization function.

The neural network may be learned based on the Mumford-Shah function-based loss function and a loss function using pixel-unit labels.

The segmenting unit may output a segmentation map for the received image by using the neural network and may segment the received image by using the output segmentation map.

The segmenting unit may output a segmentation map, to which a bias value of the received image is reflected, by using the neural network and may segment the received image by using the output segmentation map.

The Mumford-Shah function-based loss function may be a loss function that performs computation using only an input image without a label.

The neural network may include a convolution framelet-based neural network and a neural network including a pooling layer and an unpooling layer.

BRIEF DESCRIPTION OF THE FIGURES

The above and other objects and features of the present disclosure will become apparent by describing in detail embodiments thereof with reference to the accompanying drawings.

DETAILED DESCRIPTION

Figure 1:
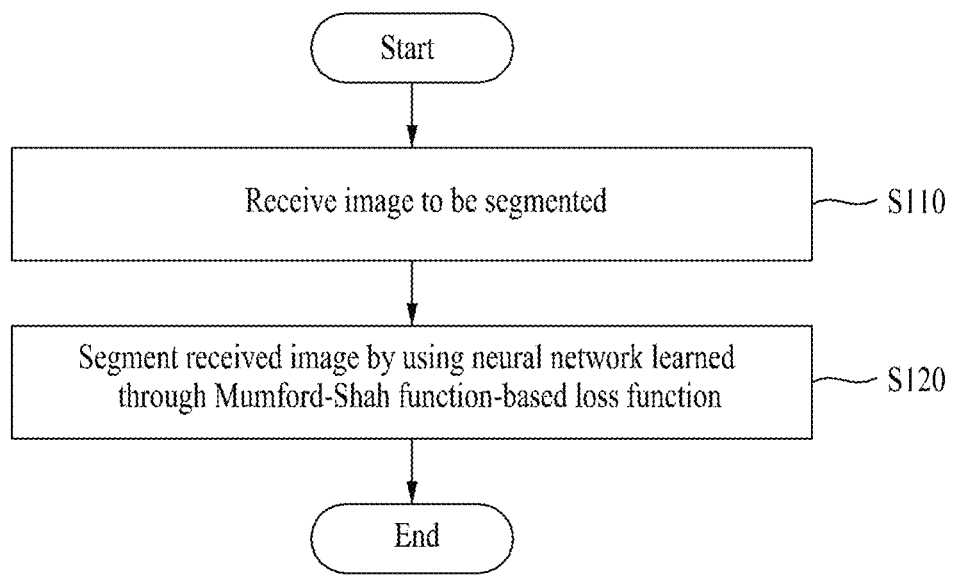
FIG. 1 is an operation flowchart illustrating an image segmentation method, according to an embodiment of the present disclosure.

The above and other aspects, features and advantages of the present disclosure will become apparent from the following description of the following embodiments given in conjunction with the accompanying drawings. The present disclosure, however, may be embodied in various different forms, and should not be construed as being limited only to the illustrated embodiments. Rather, these embodiments are provided as examples so that the present disclosure will be thorough and complete, and will fully convey the concept of the present disclosure to those skilled in the art. The present disclosure may be defined by scope of the claims. Meanwhile, the terminology used herein to describe embodiments of the present disclosure is not intended to limit the scope of the present disclosure.

The terms used herein are provided to describe the embodiments but not to limit the present disclosure. In the specification, the singular forms include plural forms unless particularly mentioned. The terms "comprises" and/or "comprising" used herein does not exclude presence or addition of one or more other components, steps, operations, and/or elements in addition to the aforementioned components, steps, operations, and/or elements.

Unless otherwise defined, all terms (including technical and scientific terms) used herein have the same meaning as commonly understood by those skilled in the art to which the present disclosure pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

Hereinafter, the best embodiments of the present disclosure will be described in detail with reference to accompanying drawings. The same reference numerals are used for the same components in the drawings and redundant explanations for the same components are omitted.

According to embodiments of the present disclosure, real-time image segmentation may be possible by using a neural network, and the image segmentation performance may be improved, by learning a neural network by using a Mumford-Shah function-based loss function capable of being used for deep learning-based image segmentation with no labeled data or the small amount of labeled data One of the most important contributions of the present disclosure is image segmentation based on a neural network (e.g., CNN), in particular, in a situation where training data is not sufficient. Specifically, the present disclosure may use the Mumford-Shah function-based loss function capable of being easily adopted for a segmentation algorithm based on a neural network, for example, CNN.

Because the Mumford-Shah function is based on pixel similarity, a Mumford-Shah function-based loss function may use complementary information about semantic information used in a conventional CNN-based segmentation algorithm. In detail, to set up a supervised learning, the loss function of the present disclosure may be used as a new regularization function for improving the performance of a neural network in consideration of the pixel similarity. Also, it is understood that the Mumford-Shah function is a self-supervised loss. Accordingly, semi-supervised or unsupervised learning based on CNN may be easily obtained without ground-truth labels or bounding box annotations. Moreover, when intensity inhomogeneities are present, the Mumford-Shah function for unsupervised segmentation may be modified to include the correction of a bias region.

Because of the similarity between the characteristic function of the Mumford-Shah function and the softmax layer output function used in a neural network, the present disclosure may directly minimize the Mumford-Shah function. This minimization may be made in a data-centric method using a deep neural network, which is capable of being computed in real time.

Furthermore, the neural network used in the present disclosure may include a convolution framelet-based neural network and a neural network (e.g., U-Net) including a pooling layer and an unpooling layer. In addition, the neural network used in the present disclosure may include various types of neural networks applicable to the present disclosure.

The convolution framelet refers to a method of expressing an input signal through a local base and a non-local base. To reveal the black box features of a deep convolutional neural network, the convolution framelet is described in detail in the study (Ye, J C., Han, Y., Cha, E.: Deep convolutional framelets: a general deep learning framework for inverse problems. SIAM Journal on Imaging Sciences 11(2), 991-1048(2018)) of new mathematical theories of deep convolution framelet.

FIG. 1 is an operation flowchart illustrating an image segmentation method, according to an embodiment of the present disclosure.

Referring to FIG. 1, according to an embodiment of the present disclosure, an image segmentation method receives an image to be segmented (S110).

Herein, the image to be segmented may include all types of images such as an image including an object, a medical image, and the like.

When the image is received in operation S110, the method segments the received image by using a neural network learned through a Mumford-Shah function-based loss function (S120).

Herein, the neural network may be learned based on one of supervised learning, semi-supervised learning, and unsupervised learning. When the neural network is learned by the supervised learning, the Mumford-Shah function-based loss function may be used as a regularization function. When the neural network is learned by the semi-supervised learning or the unsupervised learning, the Mumford-Shah function-based loss function may be used as a loss function.

Moreover, the neural network may be learned based on a Mumford-Shah function-based loss function and a loss function (e.g., a cross entropy function) using a pixel-unit label.

At this time, in operation S120, the method may output a segmentation map for the received image by using a neural network and then may segment the received image by using the output segmentation map. Furthermore, the method may output a segmentation map, to which a bias value of the received image is reflected, by using a neural network and then may segment the received image by using the output segmentation map.

Such the Mumford-Shah function-based loss function may be a loss function that performs computation using only an input image without labels.

The neural network used in the method of the present disclosure may include a convolution framelet-based neural network and a neural network (e.g., U-Net) including a pooling layer and an unpooling layer.

The method according to an embodiment of the present disclosure will be described in detail with reference to FIGS. 2 to 6 as follows.

Variable Image Segmentation

A conventional variable approach regards image segmentation as a clustering problem. Representative examples include k-means, moving averages, normalized cuts, graph cuts, level-sets, and the like. Such the approach generally minimizes an energy function. For example, one of the most well-known energy functions is the Mumford-Shah function. In particular, a Mumford-Shah energy function for image segmentation in a given image measurement "x(r) (r∈Ω⊂R$^2$)" may be defined in Equation 1 and Equation 2 below.

$$\mathcal{L}_{MS}(\chi; x) = \varepsilon(\chi, x) + \lambda \sum_{n=1}^{N} \int_{\Omega} |\nabla \chi_n(r)| dr \quad \text{[Equation 1]}$$

$$\varepsilon(\chi, x) = \sum_{n=1}^{N} \int_{\Omega} |x(r) - c_n|^2 \chi_n(r) dr \quad \text{[Equation 2]}$$

Herein, $\chi_n(r)$ may denote a characteristic function of the n-th class as shown in Equation 3 below. $c_n$ may denote an average pixel value given by Equation 4 below.

$$\sum_{n=1}^{N} \chi_n(r) = 1, \forall r \in \Omega \quad \text{[Equation 3]}$$

$$c_n = \frac{\int_{\Omega} x(r) \chi_n(r) dr}{\int_{\Omega} \chi_n(r) dr} \quad \text{[Equation 4]}$$

For multi-channel images such as color images, this energy function may be easily extended when x(r) and $c_n$ are defined as vectors composed of each channel value.

For an image having intensity inhomogeneities, a pixel within the same region may be significantly changed not to be allocated to a single constant value. To this end, a conventional local intensity clustering method of alleviating a piecewise constant assumption as described in Equation 5 has been proposed.

$$x(r) \simeq b(r) \sum_{n=1}^{N} c_n \chi_n(r) \quad \text{[Equation 5]}$$

Herein, b(r) may denote a bias region (or a field) that is slowly changed. Equation 2 may be expressed in Equation 6 below.

$$\varepsilon(\chi, x, b) = \int \left( \sum_{\omega \in I} \int_{\Omega} K(r-r') ||x(r') - b(r)(c_\omega)||^2 \chi_\omega(r') dr' \right) dr \quad \text{[Equation 6]}$$

Herein, K(r–r') may denote a kernel function. Truncated Gaussian function may be used for kernel function K. The bias region b(r) and a class label {$c_n$} are simultaneously estimated together when the energy function is minimized. Accordingly, this method enables image segmentation through the correction of intensity inhomogeneities.

Unfortunately, the Mumford-Shah function and the biased scalability are not differentiable due to the characteristic function $\chi_n$. The conventional technology has proposed a multiphase level setting method such that a cost function is capable of being differentiable. Specifically, a set "Φ=[φ$_1$ . . . φ$_p$]" may be considered. Herein, "φ$_i$:Ω→R" may denote a level function in an image domain Ω for an actual number indicating the height of a level set. In the corresponding technology, a vector Heaviside function is defined in Equation 7 below.

$$H(\Phi) = |H(\phi_1) \ldots H(\phi_p)| \quad \text{[Equation 7]}$$

Herein, when "Φ>0", H(Φ)=1; otherwise, H(Φ)=0. "N:=2$^p$" indicating N unique classes in Ω may be generated by generating the possibility of a value of the vector Heaviside function by using this definition.

This leads to the Euler-Lagrangian equation for a level function. For example, for "N=4" level classification having two level functions, for example, "p=2" and "N={00, 01, 10, 11}", the Euler-Lagrangian equation for a level function may be provided by Equation 8 and Equation 9 below.

$$\frac{\partial \phi_1}{\partial t} = \quad \text{[Equation 8]}$$
$$\delta_\varepsilon(\phi_1)\left\{\lambda div\left(\frac{\nabla \phi_1}{|\nabla \phi_1|}\right) - [((x-c_{11})^2 - (x-c_{01})^2)H(\phi_2) + \right.$$
$$\left. ((x-c_{10})^2 - (x-c_{00})^2)(1-H(\phi_2))]\right\}$$

$$\frac{\partial \phi_2}{\partial t} = \quad \text{[Equation 9]}$$
$$\delta_\varepsilon(\phi_2)\left\{\lambda div\left(\frac{\nabla \phi_2}{|\nabla \phi_2|}\right) - [((x-c_{11})^2 - (x-c_{10})^2)H(\phi_1) + \right.$$
$$\left. ((x-c_{01})^2 - (x-c_{00})^2)(1-H(\phi_1))]\right\}$$

Herein, δε may denote an approximation to the one-dimensional Dirac delta function derived from the differentiation of the Heaviside function. The multiphase level setting approach may successfully segment spatially-separated regions of the same class thanks to the high-level lifting characteristics of a level function.

CNN-Based Image Segmentation

1) Supervised semantic segmentation: When a label in a semantic pixel scheme is used, a deep neural network approach has become a main segmentation scheme thanks to the high performance and fast runtime complexity. Because fully convolutional networks (FCNs) generates an output map in which inputs have the same size as one another, various deep learning methods using FCN have been studied for semantic image segmentation.

2) Weak/semi-supervised semantic segmentation: A supervised learning method provides high-performance semantic segmentation. However, it is difficult to obtain a large amount of data for an image having a pixel-level label. To solve the issues, a method of integrating semantic segmentation and object localization has been proposed with only image-unit labels. In addition, a prediction maximization (EM) method of predicting the segmentation map by using the label of the image unit has also been proposed. Besides, a detachable architecture for separately learning classification and segmentation networks has been proposed by using data with image-unit labels and pixel-unit labels. Alternatively, an adversarial generative learning method for image segmentation has also been proposed.

3) Unsupervised segmentation: An unsupervised learning method has also been studied to segment image data without a ground-truth segmentation mask. Several studies have recently suggested an unsupervised approach using a classical optimization-based algorithm as a constraint function.

The main goal of the present disclosure is used to utilize the Mumford-Shah function together with a neural network approach, which contributes as follows.

(1) In a method of the present disclosure, the Mumford-Shah function is directly minimized by using a neural network by back-propagation in contrast to a conventional multiphase level setting approach, which computationally relies on the evolution of an expensive level function by Euler-Lagrangian equation.

(2) Unlike the conventional weak/semi-supervised segmentation, the method according to an embodiment of the present disclosure does not require a weak supervision for unlabeled data. However, these unlabeled images are used as elements of training data thanks to the Mumford-Shah function which relies on pixel statistics. Accordingly, the method of the present disclosure may greatly alleviate a manual labeling task.

(3) A conventional CNN-based unsupervised learning method generally requires complex pre-processing and/or post-processing. However, the method according to an embodiment of the present disclosure does not need the post-processing and only needs to add a Mumford-Shah loss function to the conventional CNN approach.

(4) A combination of level-set method and CNN segmentation is trained in a manner of supervising or weak supervising a network. Afterward, the level-set method is used in the refinement phase of the segmentation map. On the other hand, the method according to an embodiment of the present disclosure may be used to train a neural network for semi-supervised, unsupervised, and supervised learning by directly minimizing the Mumford-Shah function.

(5) When the Mumford-Shah function-based loss function in the present disclosure is used as a data adaptive regularization function in a supervised segmentation method, the network may better adapt to specific image statistics, and thus the loss function may further improve the segmentation performance.

In the present disclosure, the softmax layer of a neural network (e.g., CNN) may be used as a differentiable function of the characteristic function such that the Mumford-Shah function is capable of being directly minimized. This is different from a conventional multiphase level set method of obtaining a differentiable energy function that approximates a characteristic function by using a vector Heaviside function of the multiphase level set.

In detail, the n-th channel softmax output from a neural network may be expressed in Equation 10 below.

$$y_n(r) = \frac{e^{z_n(r)}}{\sum_{i=1}^{N} e^{z_i(r)}}, n = 1, 2, \ldots, N \qquad [\text{Equation 10}]$$

Herein, $r \in \Omega$. $z_i(r)$ may denote a network output at 'r' in a preceding layer before softmax.

When the pixel value of 'r' belongs to class 'n', the output value of Equation 10 is close to 1. Moreover, the output value in Equation 10 is basically the same as an attribute of the characteristic function in Equation 3, and thus may be expressed in Equation 11 below.

$$\sum_{n=1}^{N} y_n(r) = 1, \forall r \in \Omega \qquad [\text{Equation 11}]$$

This similarity means that the output of the softmax function is capable of operating as a differentiable approximation value of the characteristic function for class membership.

Accordingly, the Mumford-Shah function-based loss function in the present disclosure may be expressed in Equation 12 below.

$$\mathcal{L}_{MScnn}(\Theta; x) = \qquad [\text{Equation 12}]$$
$$\sum_{n=1}^{N} \int_{\Omega} |x(r) - c_n|^2 y_n(r) dr + \lambda \sum_{n=1}^{N} \int_{\Omega} |\nabla y_n(r)| dr$$

Herein, $x(r)$ denotes an input; $y_n(r) := y_n(r; \Theta)$ may denote an output of the softmax layer in Equation 10; and $c_n$ may denote an average pixel value of the n-th class. $c_n$ may be expressed in Equation 13 below.

$$c_n := c_n(\Theta) = \frac{\int_{\Omega} x(r) y_n(r; \Theta) dr}{\int_{\Omega} y_n(r; \Theta) dr} \qquad [\text{Equation 13}]$$

Herein and $\Theta$ may denote a network parameter that is capable of being learned.

Equation 12 may be different with respect to $\Theta$. Accordingly, the loss function in Equation 12 may be minimized through back-propagation during training. Another feature of the loss function is used to provide self-supervised loss for segmentation. This attribute is useful for an unsupervised segmentation method to which a label-based supervised loss function is incapable of being applied. Furthermore, even when a semantic label is capable of being used, this loss function may induce image segmentation based on the distribution of pixel values capable of being augmented.

The given cost function (i.e., for Equation 12, a standard method of the variable approaching scheme) is used to solve the Euler-Lagrangian equation as shown in Equation 14 below.

$$-\lambda \nabla \cdot \left(\frac{\nabla y_n}{|\nabla y_n|}\right) + (x(r) - c_n)^2 - \sum_{i \neq n}(x(r) - c_i)^2 = 0 \quad \text{[Equation 14]}$$

For all n, the last term may come from constraints in Equation 11. The corresponding fixed-point iteration for obtaining a solution of the Euler-Lagrangian equation may be expressed in Equation 15 below.

$$y_n^{k+1} = y_n^k \left| \eta^k \left( \lambda div\left(\frac{\nabla y_n^k}{|\nabla y_n^k|}\right) \right) \sum_{i=1}^{N} (1)^{\delta(n,i)} (x(r) c_i^k)^2 \right| \quad \text{[Equation 15]}$$

Herein, the superscript 'k' may denote the k-th iteration; $\delta(n, i)$ may denote a discrete Dirac delta function; and, $\eta^k$ may denote a step size.

Figure 2:
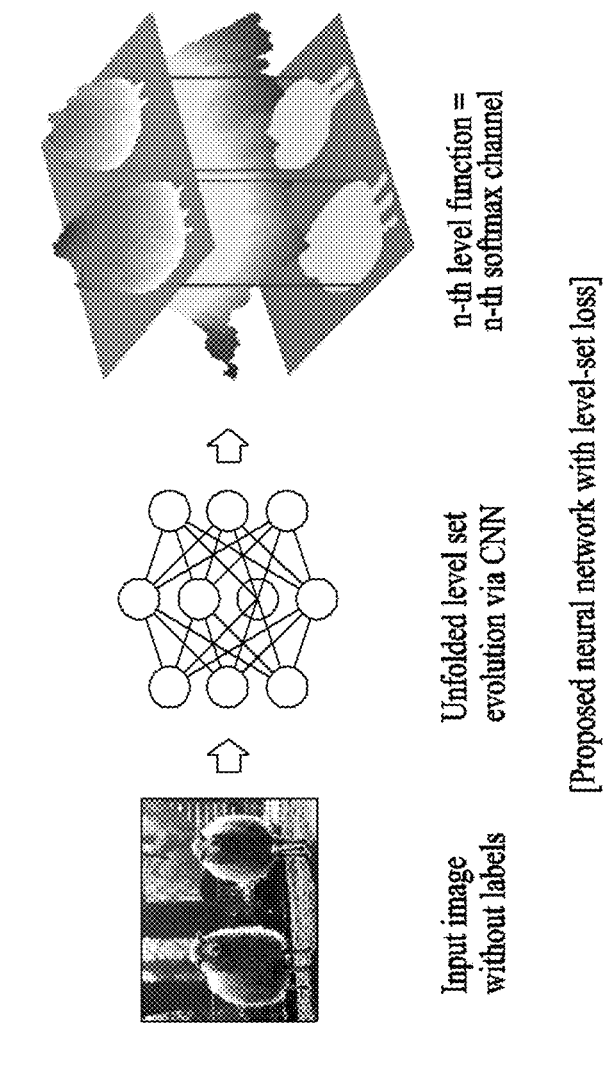
FIG. 2 illustrates a view for comparing a level-set method and a method of the present disclosure.

The neural network according to an embodiment of the present disclosure may be interpreted as the unrolled iteration in Equation 15, which is truncated by the specific number of iterations, which may explain the unsupervised segmentation problem through the comparison with a level-set method as shown in FIG. 2.

In FIG. 2, the level-set method may segment a region corresponding to a specific threshold value (i.e., a specific level), by using an energy minimization function used in a level-set method for the distribution of pixels constituting an image. Herein, multiple specific levels may be present. In comparison, according to an embodiment of the present disclosure, when receiving an image without labels, the neural network learned based on the Mumford-Shah function may automatically generate 'n' segmentation maps. This segmented image may be 'n' levels generated by the conventional level-set method.

Figure 3A:
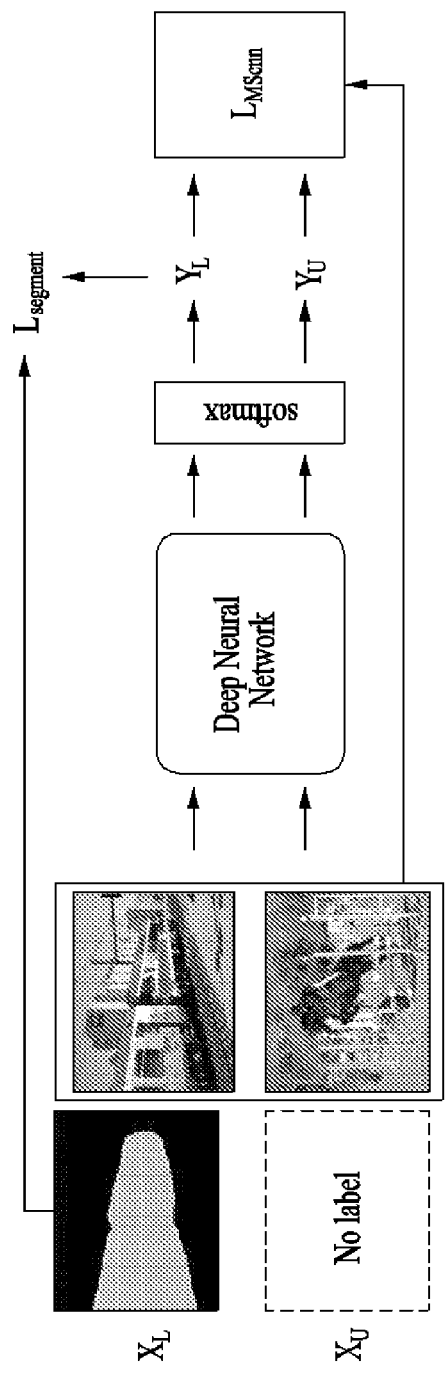
FIGS. 3A and 3B illustrate views for describing an image segmentation process by using a method of the present disclosure.
Figure 3B:
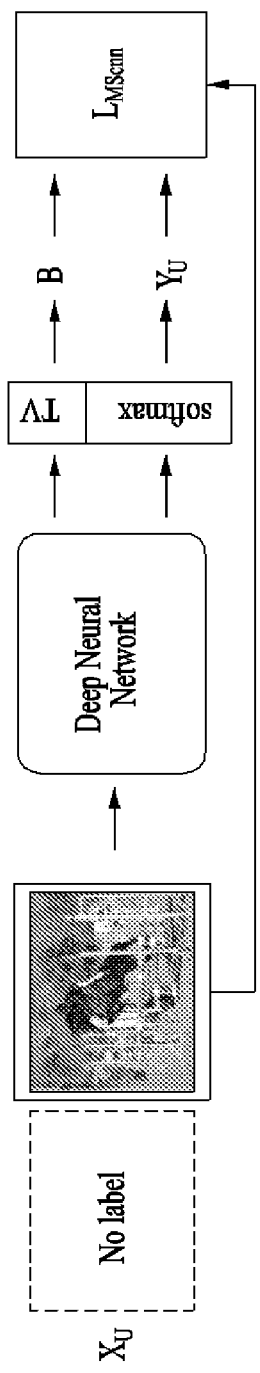

The Mumford-Shah function-based loss function (or the Mumford-Shah loss function) may be combined with supervised, semi-supervised, and unsupervised segmentation algorithms. Specifically, FIGS. 3A and 3B illustrate general uses of a loss function for semi-supervised and unsupervised segmentation tasks, respectively. Herein, a deep neural network may be a conventional segmentation network. This segmentation network receives images of data with or without pixel-level labels and generates a segmentation map. The only difference is used to add $L_{MScnn}$ that is the Mumford-Shah loss function.

Hereinafter, various applications of the Mumford-Shah loss function will be described in more detail.

1) When the semantic label is present: As shown in FIG. 3A, according to an embodiment of the present disclosure, when there are some pixel-level semantic labels in a segmented dataset, the deep neural network may be estimated or may be learned without weak supervised labels by applying a conventional segmentation loss function ($L_{segment}$) to pixel-level labeled data or applying a Mumford-Shah loss function ($L_{MScnn}$) to data without labels. Especially, to use both labeled data and unlabeled data, the loss function of network training may be designed as shown in Equation 16 below.

$$\text{loss} = \alpha \mathcal{L}_{segment} + \beta \mathcal{L}_{MScnn} \quad \text{[Equation 16]}$$

$$\alpha = \begin{cases} 1, & \text{if the input has labels} \\ 0, & \text{otherwise} \end{cases}$$

Herein, β may denote a hyper-parameter. $L_{segment}$ may generally mean a cross entropy function, and may be expressed in Equation 17 below.

$$\mathcal{L}_{CE} = \frac{1}{P} \sum_{i=1}^{P} \sum_{n=1}^{N} g_n(i) \log y_n(i) \quad \text{[Equation 17]}$$

Herein, $y_n(i)$ may denote the predicted probability of pixel 'i' belonging to class 'n' in a segmentation map. $g_n(i)$ may denote a semantic label. 'P' may denote the number of input pixels.

Accordingly, when the network receives unlabeled input per pixel, the network is trained only with the Mumford-Shah loss function. Otherwise, the network is trained to segment a specific region and to classify such categories by using both the Mumford-Shah loss and the conventional segmentation loss.

In the meantime, when a complete pixel-wise semantic label is present, it may be set to "α=1" during the entire network training. However, unlike the conventional supervised learning method that minimizes $L_{segment}$, the neural network according to an embodiment of the present disclosure is trained by using both $L_{segment}$ and $L_{MScnn}$ so as to perform segmentation in more detail in consideration of pixel similarity and semantic information.

2) When there is no semantic label: Because a loss in the present disclosure is a self-supervised loss, a cluster based on pixel statistics may be estimated by setting "α=0" in Equation 16 in the unsupervised image segmentation. However, the Mumford-Shah function may simply force respective segmentation to have a pixel value similar to the normalization of a contour length. When an image pixel value within each region significantly fluctuates due to intensity inhomogeneities, a separate segmentation region may be frequently generated. An additional semantic loss function may assist the problem so as to be alleviated. However, such additional supervision is impossible in unsupervised learning. In this regard, the above-described estimation of a bias region may provide additional supervised information.

Specifically, in Equation 6, constraints that the total variation of a bias region is small are imposed such that the delta function kernel "K(r-r')=δ(r-r')" is capable of being selected. Afterward, Equation 12 may be expressed in Equation 18 below.

$$\mathcal{L}_{MScnn}(\Theta; x) = \sum_{n=1}^{N} \int_{\Omega} |x(r) - b(r)c_n|^2 y_n(r)dr + \lambda \sum_{n=1}^{N} \int_{\Omega} |\nabla y_n(r)| dr + \gamma \int_{\Omega} |\nabla b(r)| dr \quad \text{[Equation 18]}$$

Herein, γ>0 may denote a fixed parameter. $c_n$ may be expressed in Equation 19 below.

$$c_n = \frac{\int_\Omega b(r)x(r)y_n(r)dr}{\int_\Omega b^2(r)y_n(r)dr} \quad \text{[Equation 19]}$$

The center $c_n$ is calculated by using the estimated bias in addition to the input image x(r). Accordingly, the neural network may simultaneously estimate both a bias region and a segmentation map by minimizing the loss function in Equation 18.

As shown in FIG. 3B, a bias region may be easily estimated in a neural network. Specifically, in addition to $\{z_n(r)\}$ in Equation 10 provided to the softmax layer, the neural network may be designed to output an additional bias region $b_n(r)$. When a bias region channel before the softmax layer is simply increased and the loss function in Equation 18 is minimized, both a bias and a bias correction segmentation mask may be obtained by the same neural network.

Dataset

1) PASCAL VOC 2012: PASCAL VOC 2012 segmentation benchmark consisting of 20 object classes for natural images captured in daily life, may be used to evaluate the semantic segmentation performance for the model of the present disclosure. In addition, a training dataset consisting of 10,582 images may be obtained by additionally using a label image of the segmentation boundaries dataset (SBD) to training. Accordingly, the semi-supervised algorithm for verification may be evaluated by using 1449 images.

2) LiTS 2017: Liver tumor segmentation (LiTS) dataset may be used to apply the present disclosure to medical image segmentation. In this way, contrast-enhanced 3D abdominal CT scans of liver and tumor sites, which have a resolution of 512×512 pixels in each axial slice, and 201 segmentation labels may be provided. However, 70 scans among 201 datasets do not have a ground-truth label. Accordingly, only 131 scans, to which a semantic label (i.e. liver and tumor) is provided in units of pixels, may be used. Among 131 scans provided together with ground-truth labels, 118 scans may be used for network training, and 13 scans may be used in an inference phase. To ignore irrelevant details, an intensity value for a range [−124, 276] HU may be fixed; an image may be normalized to [0, 1] by dividing the image by the maximum value of the data; alternatively, the image may be down-sampled to a resolution of 256×256.

3) BRATS 2015: The Multimodal Brain Tumor Image Segmentation Benchmark (BRATS) includes 274 MR scans in various patient-historical diagnoses. There are four MRI sequences such as T1-weight (T1), gadolinium-enhanced contrast (T1c), T2-weight (T2), and FLAIR in each scan, which are images in each of which a skull is stripped. All training data having a size of 240×240×155 have manual segmentation labels for various brain tumors. A deep neural network may be trained to complete tumor segmentation by using 249 pieces of training data. The neural network of the present disclosure may be evaluated by using 25 test sets.

4) BSDS500: Berkeley Segmentation Data Set and Benchmarks 500 (BSDS500) may provide human-annotated labels with 200 color (RGB) images for training, 100 color (RGB) images for validation, and the rest 200 color (RGB) images for test. The sizes of all training images may be adjusted to 512×512×3 as needed.

Implementation Detailed Information

When there is a pixel-level semantic label in a dataset, a deep neural network may be trained in a semi-supervised scheme. Otherwise, the network may be trained in an unsupervised environment.

1) Segmentation of semi-supervised objects in natural images: To evaluate a proposed Mumford-Shah loss by using the PASCAL VOC 2012 dataset, two semi-supervised segmentation models of SSGAN and AdvSemi may be adopted, and the network may be trained in a semi-supervised environment regardless of loss. The modified version of DeepLab-v2 may be used as a default network. This modified DeepLab-v2 uses the Atrous Spatial Pyramid Pooling (ASPP) method in the last layer without using multi-scale fusion.

For a fair comparison, the same parameter may be used between a comparison method and a method of the present disclosure other than the final output of the softmax operation to calculate a loss function. After an image is randomly scaled to 321×321 so as to be truncated, all models may be trained by using two graphic cards of NVIDIA GeForce GTX 1080 Ti.

2) Segmentation of semi-supervised tumors in medical images: A modified U-Net may be used for tumor segmentation in LiTS 2017 and BRATS 2015. These modifications come from the pooling and unpooling layers of U-Net using lossless decomposition. That is, four adjacent pixels thus input are decomposed into four pieces of channel data having the reduced size in a pooling layer. On the other hand, four channels thus reduced are grouped into a single expanded channel in the pooling layer. Lossless correction may improve segmentation performance by maintaining a lot of details.

Three adjacent slices may be stacked as inputs. The network may be trained to generate a segmentation mask corresponding to a central slice of an input. At this time, the present disclosure may use an Adam optimization method. For each of LiTS dataset and BRATS dataset, an initial learning rate is set to $10^{-5}$ and $10^{-4}$ and is multiplied by 0.5 for respective 20 epochs. The present disclosure may train models having a batch size of 4 at 50 epochs and 40 epochs of a dataset, respectively.

3) Unsupervised segmentation in natural images: A method of the present disclosure simply replaces a semantic loss with a Mumford-Shah loss. Accordingly, the method of the present disclosure may convert a conventional supervised segmentation network into an unsupervised network. To this end, the present disclosure employs U-Net and may train a model without ground-truth labels on the BSDS500 dataset. Furthermore, to show that a conventional unsupervised segmented network is capable of being improved, the loss function of the present disclosure may train an unlabeled network by adding the loss function of the present disclosure to a Backprop model. In U-net training, an Adam optimization algorithm having an initial learning rate of $10^{-4}$ and a batch size of 4 may be used. Training may be stopped after 700 epochs. An SGD algorithm may be used for the training of the modified Backprop. Parameters may be initialized through Xavier initialization.

Figure 4:
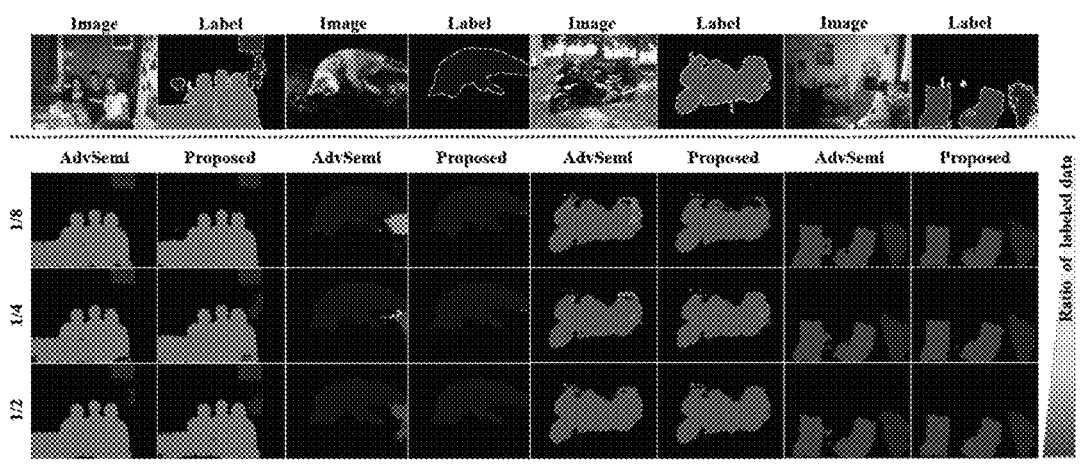
FIG. 4 illustrates a view for comparing a semi-supervised segmentation result by a conventional method with a semi-supervised segmentation result by a method of the present disclosure.

FIG. 4 illustrates a view for comparing a semi-supervised segmentation result by a conventional method with a semi-supervised segmentation result by a method of the present disclosure. FIG. 4 illustrates a segmentation result by AdvSemi and a method of the present disclosure by using semi-supervised learning including ½, ¼, or ⅛ labeled data.

As understood through FIG. 4, it may be seen that a method of the present disclosure shows a more accurate segmentation result than a conventional method as the amount of labeled data increases. In other words, it may be seen that better segmentation results even in semi-supervised learning are shown when a Mumford-Shah loss-based neural network of the present disclosure is used.

Figure 5:
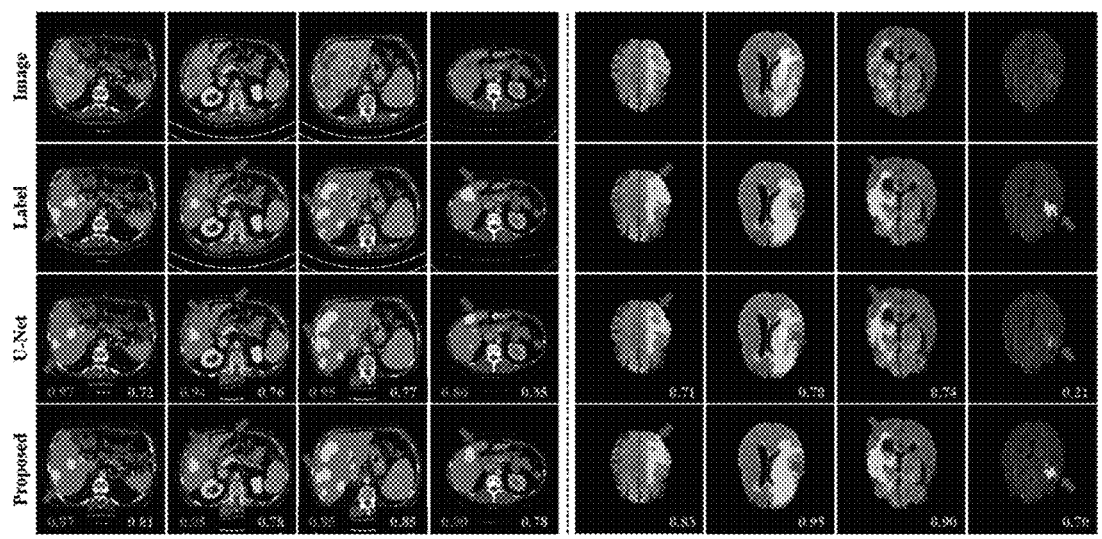
FIG. 5 illustrates a view of a semi-supervised tumor segmentation result by a method of the present disclosure.

FIG. 5 illustrates a view of a semi-supervised tumor segmentation result by a method of the present disclosure. A left side in FIG. 5 illustrates a segmentation result when 1/10 labeled data is used in a LiTS dataset. A right side in FIG. 5 illustrates a segmentation result when ¼ labeled data is used in a BRATS dataset.

The first row in FIG. 5 indicates a central slice of an input. The second row in FIG. 5 indicates a ground-truth label. The third row in FIG. 5 indicates a result by the supervised learning method of $L_{CE}$. The fourth row in FIG. 5 indicates a result of semi-supervised learning using $L_{CE}$ and $L_{MScnn}$ of the present disclosure. A score at a lower end indicates a dice score.

As understood through FIG. 5, it may be seen that the Mumford-Shah loss-based neural network is capable of detecting boundaries of tumor regions in more detail. Besides, an original deep neural network may generate a segmentation map having an intersection over-union (IoU) score of less than 0.5. However, in the same network, the loss function of the present disclosure may improve the result having an IoU score higher than 0.7. That is, it may be seen that small and thin tumors that are difficult to distinguish from the surrounding regions may be clearly segmented in the method of the present disclosure because a Mumford-Shah loss function is computed with pixel-level information.

Figure 6:
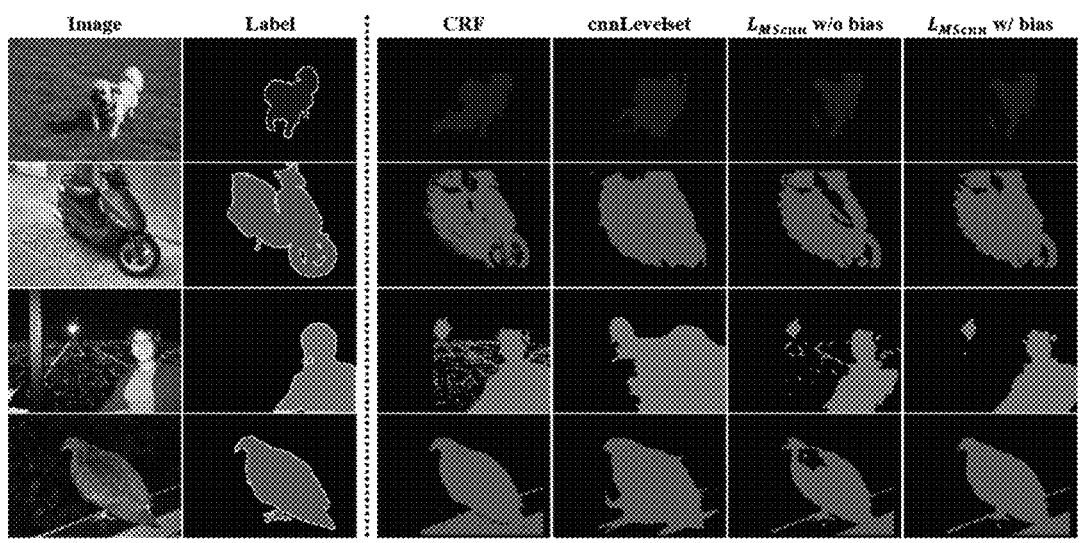
FIG. 6 illustrates a view of an unsupervised segmentation result according to a bias value by a method of the present disclosure.

FIG. 6 illustrates a view of an unsupervised segmentation result according to a bias value by a method of the present disclosure. FIG. 6 illustrates cnnLevelset and CRF segmentation methods and segmentation results for a case that a bias value is reflected to the present disclosure and a case that a bias value is not reflected to the present disclosure.

As understood through FIG. 6, it may be seen that cnnLevelset generates very large segmentation having little details, and CRF generates detailed edge information far from object semantics. On the other hand, it may be seen that the method of the present disclosure provides a suitable balance between the two approaches for generating a segmentation map associated with object semantics. Moreover, the method of the present disclosure generates a segmentation map with much shorter computation time, and corrects unnecessary details when the bias value is reflected. Accordingly, it may be seen that it helps to segment complex foreground objects in images. That is, when it is difficult to segment an object such as a natural image, the method of the present disclosure may estimate a bias value of the image by using a Mumford-Shah loss function, and then may reflect the estimated bias value, thereby more accurately segmenting objects in an image such as natural images.

As such, the method according to an embodiment of the present disclosure may segment an image by using a neural network learned through a Mumford-Shah function-based loss function, thereby improving image segmentation performance and segmenting an image in real time.

Furthermore, the method according to an embodiment of the present disclosure may provide an image segmentation method based on semi-supervised learning or unsupervised learning that performs network learning on a small amount of labeled data or data without labels. Accordingly, image segmentation performance may be improved as compared to the conventional image segmentation method. In addition, when the Mumford-Shah function-based loss function used in the method of the present disclosure is applied to supervised learning, the corresponding loss function is used as a regularization function. Accordingly, the performance of the neural network may be improved by calculating the similarity of pixel values.

In addition, in the method according to the embodiments of the present disclosure, the output value obtained by passing through the softmax layer of a neural network is similar to a characteristic function in the Mumford-Shah function, and thus network learning is possible through the minimization of the Mumford-Shah function value. Because this is a data-centric scheme using a deep neural network, real-time calculations are possible on new test data.

The method according to an embodiment of the present disclosure may be applied to recognize buildings, roads, people, and cars in an image and to segment the corresponding region, in a field of computer vision. In this way, the present disclosure may be applied to autonomous driving research in satellite images. Besides, the present disclosure may be applied to research on the recognition of a human face, fingerprint, and iris. In a field of medical imaging, the present disclosure may also be applied to research of detecting a location, size, and shape in a specific region such as anatomical structures and tumors in images such as CT, MRI, and X-ray.

Figure 7:
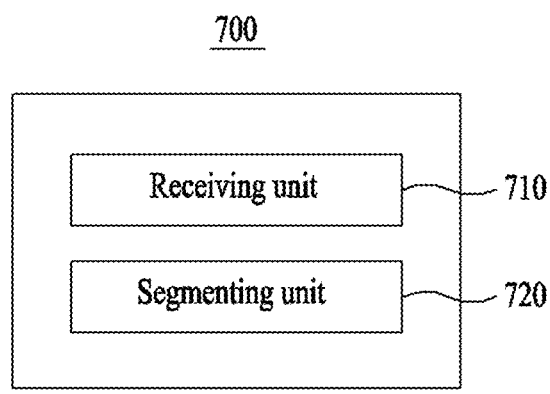
FIG. 7 illustrates a configuration of an image segmentation apparatus according to an embodiment of the present disclosure.

FIG. 7 illustrates a configuration of an image segmentation apparatus according to an embodiment of the present disclosure. FIG. 7 illustrates a conceptual configuration of an apparatus for performing the method of FIGS. 1 to 6.

Referring to FIG. 7, an image segmentation apparatus 700 according to an embodiment of the present disclosure includes a receiving unit 710 and a segmenting unit 720.

The receiving unit 710 receives an image to be segmented.

At this time, the receiving unit 710 may receive all types of images such as an image including an object, a medical image, and the like.

The segmenting unit 720 segments the received image by using a neural network learned through a Mumford-Shah function-based loss function.

Herein, the neural network may be learned based on one of supervised learning, semi-supervised learning, and unsupervised learning. When the neural network is learned by the supervised learning, the Mumford-Shah function-based loss function may be used as a regularization function. When the neural network is learned by the semi-supervised learning or the unsupervised learning, the Mumford-Shah function-based loss function may be used as a loss function.

Moreover, the neural network may be learned based on a Mumford-Shah function-based loss function and a loss function (e.g., a cross entropy function) using a pixel-unit label.

At this time, the segmenting unit 720 may output a segmentation map for the received image by using a neural network and then may segment the received image by using the output segmentation map. Furthermore, the segmenting unit 720 may output a segmentation map, to which a bias value of the received image is reflected, by using a neural network and then may segment the received image by using the output segmentation map.

Such the Mumford-Shah function-based loss function may be a loss function that performs computation using only an input image without labels.

Furthermore, the neural network may include a convolution framelet-based neural network and a neural network (e.g., U-Net) including a pooling layer and an unpooling layer.

Even though the description in the apparatus in FIG. 7 is omitted, it will be apparent to those skilled in the art that the configuration means constituting FIG. 7 may include all content described in FIGS. 1 to 6.

The foregoing devices may be realized by hardware elements, software elements and/or combinations thereof. For example, the devices and components illustrated in the embodiments of the present disclosure may be implemented in one or more general-use computers or special-purpose computers, such as a processor, a controller, an arithmetic logic unit (ALU), a digital signal processor, a microcomputer, a field programmable array (FPA), a programmable logic unit (PLU), a microprocessor or any device which may execute instructions and respond. A processing unit may perform an operating system (OS) or one or software applications running on the OS. Further, the processing unit may access, store, manipulate, process and generate data in response to execution of software. It will be understood by those skilled in the art that although a single processing unit may be illustrated for convenience of understanding, the processing unit may include a plurality of processing elements and/or a plurality of types of processing elements. For example, the processing unit may include a plurality of processors or one processor and one controller. Also, the processing unit may have a different processing configuration, such as a parallel processor.

Software may include computer programs, codes, instructions or one or more combinations thereof and configure a processing unit to operate in a desired manner or independently or collectively control the processing unit. Software and/or data may be embodied in any type of machine, components, physical equipment, virtual equipment, computer storage media or devices so as to be interpreted by the processing unit or to provide instructions or data to the processing unit. Software may be dispersed throughout computer systems connected via networks and be stored or executed in a dispersion manner. Software and data may be recorded in one or more computer-readable storage media.

The methods according to the above-described example embodiments may be recorded in computer-readable media including program instructions to implement various operations embodied by a computer. The computer-readable medium may also include the program instructions, data files, data structures, or a combination thereof. The program instructions recorded in the media may be designed and configured especially for the example embodiments or be known and available to those skilled in computer software. The computer-readable medium may include hardware devices, which are specially configured to store and execute program instructions, such as magnetic media (e.g., a hard disk, a floppy disk, or a magnetic tape), optical recording media (e.g., CD-ROM and DVD), magneto-optical media (e.g., a floptical disk), read only memories (ROMs), random access memories (RAMs), and flash memories. Examples of computer programs include not only machine language codes created by a compiler, but also high-level language codes that are capable of being executed by a computer by using an interpreter or the like.

While embodiments have been shown and described with reference to the accompanying drawings, it will be apparent to those skilled in the art that various modifications and variations may be made from the foregoing descriptions. For example, adequate effects may be achieved even if the foregoing processes and methods are carried out in different order than described above, and/or the aforementioned elements, such as systems, structures, devices, or circuits, are combined or coupled in different forms and modes than as described above or be substituted or switched with other components or equivalents.

Therefore, other implements, other embodiments, and equivalents to claims are within the scope of the following claims.

According to embodiments of the present disclosure, it is possible to segment an image by using a neural network learned through a Mumford-Shah function-based loss function, thereby improving image segmentation performance and segmenting an image in real time.

According to embodiments of the present disclosure, it is possible to provide an image segmentation method based on semi-supervised learning or unsupervised learning that performs network learning on a small amount of labeled data or data without labels. Accordingly, image segmentation performance may be improved as compared to the conventional image segmentation method.

The present disclosure may be applied to recognize buildings, roads, people, and cars in an image and to segment the corresponding region, in a field of computer vision. In this way, the present disclosure may be applied to autonomous driving research in satellite images. Besides, the present disclosure may be applied to research on the recognition of a human face, fingerprint, and iris. In a field of medical imaging, the present disclosure may also be applied to research of detecting a location, size, and shape in a specific region such as anatomical structures and tumors in images such as CT, MM, and X-ray. Accordingly, the present disclosure may be applied to increase the accuracy in diagnosing diseases, and planning surgery and treatment.

While the present disclosure has been described with reference to embodiments thereof, it will be apparent to those of ordinary skill in the art that various changes and modifications may be made thereto without departing from the spirit and scope of the present disclosure as set forth in the following claims.

What is claimed is:

1. An image segmentation method, the method comprising:
receiving an image to be segmented;
and segmenting the received image by using a neural network learned through a Mumford-Shah function-based loss function, wherein the segmenting includes:
outputting a segmentation map, to which a bias value of the received image is reflected, by using the neural network, wherein the Mumford-Shah function-based loss function is simultaneously modifiable to include correction of a bias region in the presence of one or more inhomogeneities; and
segmenting the received image by using the output segmentation map,
wherein the neural network is learned based on one of supervised learning, semi-supervised learning, and unsupervised learning,
wherein unsupervised learning is performed without post-processing.

2. The method of claim 1, wherein, when the neural network is learned based on supervised learning, the neural network uses the Mumford-Shah function-based loss function as a regularization function.

3. The method of claim 1, wherein the neural network is learned based on the Mumford-Shah function-based loss function and a loss function using pixel-unit labels.

4. The method of claim 1, wherein the Mumford-Shah function-based loss function is a loss function that performs computation using only an input image without a label.

5. The method of claim 1, wherein the neural network includes a convolution framelet-based neural network and a neural network including a pooling layer and an unpooling layer.

6. An image segmentation method, the method comprising:
   defining a Mumford-Shah function-based loss function;
   learning a neural network by using the defined Mumford-Shah function-based loss function;
   receiving an image to be segmented; and
   segmenting the received image by using the neural network learned through the Mumford-Shah function-based loss function, wherein the segmenting includes:
   outputting a segmentation map, to which a bias value of the received image is reflected, by using the neural network, wherein the Mumford-Shah function-based loss function is simultaneously modifiable to include correction of a bias region in the presence of one or more inhomogeneities; and
   segmenting the received image by using the output segmentation map,
   wherein the neural network is learned based on one of supervised learning, semi-supervised learning, and unsupervised learning, wherein unsupervised learning is performed without post-processing.

7. An image segmentation apparatus, the apparatus comprising:
   a receiving unit configured to receive an image to be segmented; and
   a segmenting unit configured to segment the received image by using a neural network learned through a Mumford-Shah function-based loss function, wherein the segmenting includes:
   outputting a segmentation map, to which a bias value of the received image is reflected, by using the neural network, wherein the Mumford-Shah function-based loss function is simultaneously modifiable to include correction of a bias region in the presence of one or more inhomogeneities; and
   segmenting the received image by using the output segmentation map,
   wherein the neural network is learned based on one of supervised learning, semi-supervised learning, and unsupervised learning,
   wherein unsupervised learning is performed without post-processing.

8. The apparatus of claim 7, wherein, when the neural network is learned based on supervised learning, the neural network uses the Mumford-Shah function-based loss function as a regularization function.

9. The apparatus of claim 7, wherein the neural network is learned based on the Mumford-Shah function-based loss function and a loss function using pixel-unit labels.

10. The apparatus of claim 7, wherein the segmenting unit outputs a segmentation map for the received image by using the neural network and segments the received image by using the output segmentation map.

11. The apparatus of claim 7, wherein the segmenting unit outputs a segmentation map, to which a bias value of the received image is reflected, by using the neural network and segments the received image by using the output segmentation map.

12. The apparatus of claim 7, wherein the Mumford-Shah function-based loss function is a loss function that performs computation using only an input image without a label.

13. The apparatus of claim 7, wherein the neural network includes a convolution framelet-based neural network and a neural network including a pooling layer and an unpooling layer.

* * * * *